United States Patent
Minami et al.

(10) Patent No.: US 6,841,086 B2
(45) Date of Patent: Jan. 11, 2005

(54) AQUEOUS COMPOSITION OF ALKALI METAL SALTS OF PARTIAL ALKYL ESTERS OF PHOSPHORIC ACID, METHOD FOR STABILIZATION AND A FIBER FINISH

(75) Inventors: Hajimu Minami, Yao (JP); Jun Watanabe, Yao (JP); Yoshishige Nakamura, Yao (JP)

(73) Assignee: Matsumoto Yushi-Seiyaku Co., Ltd., Osaka (JP)

( * ) Notice: Subject to any disclaimer, the term of this patent is extended or adjusted under 35 U.S.C. 154(b) by 259 days.

(21) Appl. No.: 10/105,388

(22) Filed: Mar. 26, 2002

(65) Prior Publication Data

US 2002/0153504 A1 Oct. 24, 2002

Related U.S. Application Data

(63) Continuation-in-part of application No. 10/049,062, filed as application No. PCT/JP01/04740 on Jun. 5, 2001, now abandoned.

(30) Foreign Application Priority Data

Jun. 7, 2000 (JP) ........................................ 2000-210567

(51) Int. Cl.⁷ .................... D06M 10/00; D06M 13/148; C07C 31/18; C07F 9/09; C07H 3/02

(52) U.S. Cl. ..................... 252/8.84; 252/8.85; 252/8.86
(58) Field of Search ............................... 252/8.84, 8.85, 252/8.86

(56) References Cited

U.S. PATENT DOCUMENTS 4,135,879 A * 1/1979 Hasenclever .................... 8/142
4,995,884 A 2/1991 Ross et al. .................... 8/115.6

FOREIGN PATENT DOCUMENTS

| JP | 59-223370 | 12/1984 | .......... D06M/13/32 |
| JP | 60-224867 | 11/1985 | .......... D06M/13/32 |
| JP | 60-224868 | 11/1985 | .......... D06M/13/32 |
| JP | 61-124680 | 6/1986 | .......... D06M/13/32 |

* cited by examiner

*Primary Examiner*—Hoa Van Le
(74) *Attorney, Agent, or Firm*—Sherman & Shalloway

(57) ABSTRACT

Stabilizing an aqueous solution of an alkali metal salt of partial alkyl esters of phosphoric acid by adding 1 to 10 weight percent of $C_{3-12}$ polyhydric alcohol having three or more of hydroxyl groups to an alkali metal salt of partial alkyl esters of phosphoric acid having linear of branched-chain alkyl groups of 16 to 22 average carbon number, 0.6 to 1.0 degree of phosphorylation and 60 to 100% of neutralization degree, and providing a fiber finish containing the stabilized aqueous solution as a major component.

6 Claims, No Drawings

US 6,841,086 B2

AQUEOUS COMPOSITION OF ALKALI METAL SALTS OF PARTIAL ALKYL ESTERS OF PHOSPHORIC ACID, METHOD FOR STABILIZATION AND A FIBER FINISH

CROSS REFERENCE TO RELATED APPLICATION

This application is a continuation-in-part of the application U.S. Ser. No. 10/049,062 filed Feb. 7, 2002, which is a U.S. nationalization of International Application PCT/JP01/04740 filed Jun. 5, 2001, which claims priority from Japan 2000-210567 filed Jun. 7, 2000.

FIELD OF INVENTION

The present invention provides an aqueous composition containing alkali metal salts of partial alkyl esters of phosphoric acid, stabilization method of the aqueous solution of the said alkali metal phosphate and a fiber finish containing the said aqueous solution. More precisely, the present invention provides an aqueous composition produced by adding a specific polyhydric alcohol to an aqueous solution containing high concentration of a specific alkali metal salt of partial alkyl esters of phosphoric acid for stabilizing the solution so as to eliminate great time-dependent increase of the viscosity of the aqueous solution and irregularity of its concentration, the process for the production and a fiber finish containing the composition.

PRIOR ART

Recently, yarn-spinning processes of synthetic staple fibers have been rapidly shifting toward the processes of higher production efficiency and better labor saving for the purpose of cost reduction. Especially under the current situation of energy saving, a yarn spinning finish with minimum property change under variable atmospheric and environmental conditions has been required eagerly for easy control of atmospheric condition in yarn-spinning processes.

Japanese Patent Laid Open Sho-59-223370 discloses a yarn spinning finish with minimum property change under variable atmospheric and environmental conditions, which contains an alkali metal salt of partial alkyl esters of phosphoric acid having linear or branched alkyl chains of 16 to 22 carbon numbers in average, a degree of phosphorylation ranging from 0.6 to 1.0 and a degree of neutralization ranging from 60 to 100%, as a major component. The property of the finish changes only slightly under variable atmospheric and environmental conditions and is effective for minimizing snow generation or fiber wrapping on rolls that are often found in yarn spinning processes operated under low temperature and low humidity or under high temperature and high humidity. The finish is usually provided in the form of an aqueous solution containing 30 to 50 weight percent of an alkali metal salt of partial alkyl esters of phosphoric acid.

However, such alkali metal salt of partial alkyl esters of phosphoric acid, of which property changes only slightly under the above-mentioned variable environmental conditions such as temperature and humidity condition, result in troubles such as non-uniform distribution of finish components in an aqueous solution or increased viscosity of the aqueous solution caused from time-dependent creaming of the solution or association of molecules. Because an alkali metal salt of partial alkyl esters of phosphoric acid existing in 30 to 50 weight percent in an aqueous solution has poor hydrophilicity due to its long-chain alkyl groups and its molecules dissolved in an aqueous solution is unstable due to its great molecular weight. Stabilization of finish containing such phosphate has been required because recovering separated solution of the said metal salt into uniform state is difficult and increased viscosity causes troubles in handling.

The above-mentioned property change of a finish containing the said alkali metal salt advances very slowly under normal condition and the above-mentioned troubles are rarely found during short-time storage in mild climate. But they are accelerated by drastic change of temperature, for example, a finish containing the said alkali metal salt drastically increases its viscosity and sometimes separates when stored under direct sunlight above 40° C. for two or three months. In addition, a finish containing the said alkali metal salt increases its viscosity and then coagulates through freezing when stored below −5° C. Recovering such frozen finish into fluid state is very difficult.

DISCLOSURE OF INVENTION

The object of the present invention is to provide an aqueous composition of an alkali metal salt of partial alkyl esters of phosphoric acid having superior stability during long time storage without separation or increased viscosity.

Another object of the present invention is to provide an aqueous composition of the said alkali metal salt that can easily recover its fluidity at room temperature after increasing its viscosity or freezing at low temperature.

Further object of the present invention is to provide a method for stabilizing an aqueous solution of the said alkali metal salt during long-time storage and at low temperature.

Further object of the present invention is to provide a fiber finish produced of the said aqueous composition of the present invention, which has superior stability as mentioned above.

Further object and advantage of the present invention are clearly illustrated in the following description.

According to the present invention, the above-mentioned object and advantage of the present invention are attained first, by an aqueous composition of an alkali metal salt of partial alkyl esters of phosphoric acid characterized by containing 100 parts by weight of an alkali metal salt of partial alkyl esters of phosphoric acid having the following properties (1) to (3);

(1) of which ester groups contain linear or branched alkyl groups having 16 to 22 carbon atoms in average, (2) of which degree of phosphorylation ranges from 0.6 to 1.0;

(3) and of which degree of neutralization ranges from 60 to 100%; and 1 to 10 parts by weight of $C_{3-12}$ polyhydric alcohol having three or more hydroxyl groups.

The above-mentioned object and advantage of the present invention are attained second, by a method for stabilizing an aqueous solution of an alkali metal salt of partial alkyl esters of phosphoric acid characterized by adding a $C_{3-12}$ polyhydric alcohol having three or more of hydroxyl groups to the said aqueous solution to the ratio at which 1 to 10 parts by weight of the polyhydric alcohol exists to 100 parts by weight of the said alkali metal salt, which has the following properties (1) to (3);

(1) of which ester groups contain linear or branched alkyl groups having 16 to 22 carbon atoms in average, (2) of which degree of phosphorylation ranges from 0.6 to 1.0, (3) and of which degree of neutralization ranges from 60 to 100%.

Further, the object and advantage of the present invention are attained third, by a fiber finish characterized by containing the above-mentioned aqueous composition of the present invention as a major component.

PREFERRED EMBODIMENT OF INVENTION

The alkali metal salts of partial alkyl esters of phosphoric acid of the present invention employed in the present invention has the following properties (1) to (3).

(1) The alkyl groups contained in its ester groups are either linear or branched and contain 16 to 22 carbon atoms in average.

(2) Its degree of phosphorylation ranges from 0.6 to 1.0. The degree of phosphorylation is number of phosphorus atoms equivalent to one equivalent of alkyl ester group of a partial alkyl esters of phosphoric acid and can be measured by a publicly known phosphomolybdic acid colorimetry. A fiber finish containing a alkali metal salt of partial alkyl esters of phosphoric acid having a degree of phosphorylation below 0.6 often results in fiber wrapping on rolls in yarn spinning process and a fiber finish containing an alkali metal salt of partial alkyl esters of phosphoric acid having a degree of phosphorylation above 1.0 often causes poor cohesion of fiber to be spun into yarn.

(3) Its degree of neutralization ranges from 60 to 100%. The degree of neutralization is the equivalent percentage of neutralized hydroxyl groups, in other words hydroxyl groups forming alkali metal salt, to the whole of the hydroxyl groups contained in a partial alkyl esters of phosphoric acid. An alkali metal salt of partial alkyl ester of phosphoric acid having a degree of neutralization below 60% produces a finish of poor antistaticity and poor solution stability. And an alkali metal salt of partial alkyl esters of phosphoric acid having a degree of neutralization above 100% contains excessive alkali compound that has not used for neutralization and gives adverse effect to handling of a resultant finish.

The said alkali metal salt of partial alkyl esters of phosphoric acid is the compound produced by neutralizing a partial alkyl esters of phosphoric acid, which is produced from one or more of higher alcohol having linear or branched chain and phosphoric acid, with an inorganic alkali hydroxide.

The average carbon number of the said higher alcohol is 16 to 22. A higher alcohol having a carbon number less than 16 produces an aqueous solution that changes its property significantly under varied environmental conditions such as temperature and humidity, and a higher alcohol having a carbon number greater than 22 results in unstable aqueous solution.

The preferable alkali metal salts of partial alkyl esters of phosphoric acid for attaining sufficient antistaticity and stable aqueous solution of resultant finish are lithium salts, sodium salts, and potassium salts. Most preferable are potassium salts.

The metal salts other than alkali metal salts, such as magnesium salts, calcium salts, barium salts, aluminum salts, zinc salts, iron salts, and cupper salts, are insoluble in water and beyond the scope of the present invention.

The examples of the alkali metal salts of partial alkyl esters of phosphoric acids are partially stearylated potassium phosphate, partially stearylated sodium phosphate, partially cetylated potassium phosphate, partially cetylated sodium phosphate, partially behenylated potassium phosphate, partially behenylated sodium phosphate and a mixture thereof. Among those, partially stearylated potassium phosphate is the most effective.

The polyhydric alcohol employed together with the said alkali metal salts of partial alkyl esters of phosphoric acid of the present invention must have 3 to 12 carbon atoms per molecule and those having 3 to 10 carbon atoms are preferable. A polyhydric alcohol having less than 3 carbon atoms cannot prevent separation, viscosity increase and freezing of resultant aqueous composition, while a polyhydric alcohol having more than 12 carbon atoms results in excessively viscous aqueous composition and deteriorates the performance of the major component, an alkali metal salt of partial alkyl esters of phosphoric acid.

The polyhydric alcohol must contain three or more of hydroxyl groups per molecule, preferably from 3 to 10. A polyhydric alcohol containing less than 3 hydroxyl groups per molecule cannot prevent the separation, viscosity increase and freezing of resultant aqueous composition, while a polyhydric alcohol containing more than 10 hydroxyl groups per molecule results in excessively viscous aqueous composition that deteriorates the performance of the major component, an alkali metal salt of partial alkyl ester of phosphoric acid.

The examples of the polyhydric alcohol employed for the present invention are glycerin, trimethylol propane, pentaerythritol, sorbitol, dextrose, fructose, sucrose, maltose and the mixture thereof.

The ratio of polyhydric alcohol is 1 to 10 weight percent of the alkali metal salts of partial alkyl esters of phosphoric acid, preferably 6 to 8 weight percent A ratio less than 1 weight percent is not effective to prevent separation, viscosity increase and freezing of resultant aqueous composition. On the other hand, a ratio greater than 10 weight percent results in unstable aqueous composition that causes troubles in yarn spinning process, such as fiber wrapping on rolls.

The polyalphaolefin emulsion for fiber disclosed in U.S. Pat. No. 4,995,884 is formulated by blending an antistatic agent and an emulsifier to an oil comprising polyalphaolefin. And an alkali metal phosphate is exemplified as the antistatic agent and ethoxylated $C_{11-15}$ alcohol and an ether of secondary alcohol and polyethylene glycol are exemplified as emulsifiers. Either of those emulsifiers, however, is not effective for stabilizing the alkali metal salts of partial alkyl esters of phosphoric acid similarly to the POE (3) lauryl ether presented in a Comparative example of the present invention.

It is preferable to add the polyhydric alcohol after the neutralization of the alkali metal salts of partial alkyl esters of phosphoric acid in its production process. But it is also possible to add the polyhydric alcohol to the aqueous solution of the alkali metal salts of partial alkyl esters of phosphoric acid several days after it is finished as a product.

Some salts of partial alkyl esters of phosphoric acid other than the alkali metal salts of partial alkyl esters of phosphoric acid of the present invention can be added to the alkali metal salts of partial alkyl esters of phosphoric acid of the present invention in the ratio at which the effect of the present invention is not adversely affected, for example 30 weight percent or less. The examples of such salts of partial alkyl esters of phosphoric acid are partially stearylated triethanol amine phosphate, partially laurylated potassium phosphate, partially decylated potassium phosphate and partially octylated potassium phosphate.

The aqueous composition of the present invention contains preferably 20 to 60 weight percent, more preferably 30 to 50 weight percent of an alkali metal salt of partial alkyl esters of phosphoric acid.

The application of the said stabilized aqueous composition of the present invention is not restricted within a certain range and one of the application of the aqueous composition is a major component of finishes applied to fiber.

The fibers to be applied with the finish of the present invention are natural fibers such as cotton, linen and wool, regenerated fibers such as rayon fiber, and synthetic fibers such as polyester, nylon and polypropylene fibers. Among those, the application to polyester staple fiber is especially effective.

The aqueous composition or its aqueous solution of the present invention is added to a fiber finish by 50 weight percent or more of the finish on solid portion basis. And for the purpose of improving the lubricity, antistaticity and cohesion of fiber imparted by the said fiber finish, one or more of the components selected among anionic surfactants such as lower alkyl phosphate salt other than the alkali metal salts of partial alkyl esters of phosphoric acid, alkyl sulfate salt and fatty acid soap; cationic surfactants such as quaternary alkyl ammonium salt; amphoteric surfactants such as alkyl betaine; nonionic surfactants such as polyoxyethylene alkyl ether, fatty acid polyethylene glycol ester, fatty acid polyhydric alcohol ester and polyoxyethylene alkyl amine; mineral oils such as liquid paraffin; ester oils such as alkyl fatty acid and polyoxyethylene alkyl fatty acid; paraffin and ester waxes; and silicone oils such as dimethyl silicone are usually added to the said finish. In addition, one or more of known defoamers, antiseptics and antioxidants can be added to the finish for improving its antifoaming performance, durability against bacteria and heat durability.

A fiber finish of which major component is the aqueous composition or its aqueous solution of the present invention is applied to fiber in the form of aqueous emulsion with known methods such as immersion, spray and kiss rolls.

The amount of such finish on fiber varies depending on fiber variants, fiber forms and end uses. Usually for polyester staple fiber, the solid portion of the finish is applied 0.02 to 0.30 weigh percent of fiber weight.

EXAMPLES

In Example 1, the variants of polyhydric alcohols employed in the present invention and the viscosity change of the resultant aqueous compositions are shown in Table 1.

In Example 2, the variants of polyhydric alcohols employed in the present invention and the durability against freezing and recovering from freezing of the resultant aqueous compositions are shown in Table 2.

In Example 3, the effect of the addition of polyhydric alcohols to different types of alkali metal salts of partial alkyl esters of phosphoric acids is shown in Table 3.

In Example 4, the ratio of the added polyhydric alcohol employed in the present invention and the viscosity change and the durability against freezing of the resultant aqueous composition are shown in Table 4.

In Example 5, the yarn spinning performance of the fiber finishes of the present invention is shown in Table 5.

In Example 6, the frictional performance of the fiber finishes of the present invention is shown in Table 6.

Example 1 and Comparative Example 1

Each of the additives components was added 8.0 weight percent on solid portion basis to an aqueous solution in which 35 weight percent of partially stearylated potassium phosphate was dissolved, and each of the mixture was homogenized. Then the viscosity of the resultant aqueous compositions was measured just after the homogenization and after four-week storage at −5° C. (a condition under which viscosity increase was accelerated) with rotary viscometer. The result is shown in Table 1.

The data in Table 1 shows that the aqueous composition of the present invention containing a partially stearylated potassium phosphate to which a polyhydric alcohol is added has lower viscosity than an aqueous composition to which no polyhydric alcohol is added. In addition, after the acceleration test of viscosity increase, the said aqueous composition of the present invention has also lower viscosity than an aqueous composition to which no polyhydric alcohol is added.

On the contrary, all of the aqueous compositions to which the components of Comparative Example 1 were added had similar or higher viscosity than the aqueous composition to which no additives were blended just after production and after the acceleration test of viscosity increase.

TABLE 1

| Components added | Viscosity Just after production | After 4-week storage at 5° C. |
|---|---|---|
| Example 1 | | |
| Glycerin | 895 | 1576 |
| Trimethylol propane | 910 | 1628 |
| Pentaerythritol | 924 | 1681 |
| Dextrose | 856 | 1300 |
| Fructose | 849 | 1321 |
| Sucrose | 855 | 1291 |
| Maltose | 841 | 1236 |
| Comparative Example 1 | | |
| Ethylene glycol | 1467 | 4125 |
| Propylene glycol | 1566 | 4313 |
| Ethyl alcohol | 8500 | 27860 |
| n-octyl alcohol | 9027 | 25087 |
| POE(3) lauryl ether | 13400 | 37690 |
| Urea | 2800 | 5310 |
| Sodium chloride | 8700 | 26000 |

TABLE 1-continued

| Components added | Viscosity Just after production | After 4-week storage at 5° C. |
|---|---|---|
| Butyl oleate | 14600 | 36800 |
| No addition | 1580 | 4040 |

Viscosity unit: mPa · s

Example 2 and Comparative Example 2

Each of the additive components was added 8.0 weight percent on solid portion basis to an aqueous solution in which 35 weight percent of partially stearylated potassium phosphate was dissolved and each of the mixture was homogenized. Each 100 ml of the resultant aqueous composition was transferred into a 100-ml glass bottle with screwed cap and stored in a refrigerator at −20° C. The freezing of the samples was observed every 30 minutes to check the time required for the start and the completion of their freezing.

Then the completely frozen samples were melted at room temperature and their appearance was observed. Then they were heated in a water bath and their fluidity was checked every 10° C. increase. The result in shown in Table 2.

TABLE 2

| Components added | Start of freezing (hr) | Completion of freezing (hr) | Appearance after melting at room temperature | Temperature at which fluidity recovered |
|---|---|---|---|---|
| Example 2 | | | | |
| Glycerin | 3.0 | 4.0 | Waxy solid | 65° C. |
| Trimethylol Propane | 3.0 | 4.0 | Waxy solid | 70° C. |
| Pentaerythritol | 3.0 | 4.0 | Waxy solid | 70° C. |
| Dextrose | 3.5 | 4.0 | Paste | 65° C. |
| Fructose | 3.5 | 4.0 | Paste | 65° C. |
| Sucrose | 3.0 | 4.0 | Waxy solid | 65° C. |
| Maltose | 3.5 | 4.0 | Paste | 50° C. |
| Comparative Example 2 | | | | |
| Ethylene glycol | 2.0 | 3.5 | Waxy solid | 70° C. |
| Propylene glycol | 2.0 | 3.5 | Waxy solid | 70° C. |
| Ethyl alcohol | 1.0 | 2.5 | Waxy solid | 70° C. |
| n-octyl alcohol | 1.0 | 2.5 | Waxy solid | 70° C. |
| POE(3) lauryl ether | 2.0 | 3.5 | Waxy solid | 70° C. |
| Urea | 1.5 | 2.5 | Waxy solid | 70° C. |
| Sodium chloride | 1.5 | 2.0 | Waxy solid | 70° C. |
| Butyl oleate | 2.0 | 3.0 | Waxy solid | 70° C. |
| No addition | 1.5 | 3.0 | Waxy solid | 70° C. |

The data in Table 2 shows that the aqueous composition of the present invention containing partially stearylated potassium phosphate to which a polyhydric alcohol is added freezes more slowly than an aqueous composition to which no polyhydric alcohol is added.

And the said aqueous composition of the present invention can recover its fluidity at lower temperature than an aqueous composition containing no polyhydric alcohol.

No components in Comparative Example 2 showed such effect.

Example 3 and Comparative Example 3

Each of different partially alkylated potassium phosphates was prepared into aqueous composition to which 8% of glycerin or sucrose was added. The viscosity of those compositions was checked just after preparation and after four-week storage at −5° C. (a condition under which viscosity increase was accelerated).

The durability under repeated freezing of the other samples of those compositions were tested by freezing at −20° C. for two-hour storage and by warming up completely at room temperature both of which were practiced six times repeatedly, and the appearance of those samples after repeated freezing and warming was checked. The result is shown in Table 3.

The variants and the concentration of the samples shown in Table 3 are as follows.

A: Partially stearylated potassium phosphate (0.8 degree of phosphorylation and 90% neutralization degree), 35% concentration in aqueous composition B: Partially stearylated potassium phosphate (0.7 degree of phosphorylation and 90% neutralization degree), 35% concentration in aqueous composition C: Partially stearylated potassium phosphate (0.75 degree of phosphorylation and 95% neutralization degree), 35% concentration in aqueous composition D: Partially stearylated potassium phosphate (0.8 degree of phosphorylation and 90% neutralization degree), 40% concentration in aqueous composition E: Partially stearylated and cetylated potassium phosphate, 40% concentration in aqueous composition F: Partially stearylated potassium phosphate described in the above A/Partially laurylated potassium phosphate (70:30 weight ratio), 35% concentration in aqueous composition G: Partially cetylated potassium phosphate, 40% concentration in aqueous composition H: Partially behenylated potassium phosphate, 30% concentration in aqueous composition I: Partially laurylated potassium phosphate, 50% concentration in aqueous composition J: Partially laurylated potassium phosphate, 60% concentration in aqueous composition The data in Table 3 shows that polyhydric alcohol is effective to various partially stearylated potassium phosphates produced with different conditions, to a mixture of different partial alkyl esters of potassium phosphoric acid of which alkyl groups have different carbon number and to other partially alkylated potassium phosphates having long-chain alkyl groups. Polyhydric alcohol increases the viscosity of the aqueous solution of partially laurylated potassium phosphate as shown in Comparative Example 3.

TABLE 3

| Samples | No additive | | | 8% glycerin | | | 8% sucrose | | |
|---|---|---|---|---|---|---|---|---|---|
| Example 3 | | | | | | | | | |
| A | — | — | — | 895 | 1576 | O | 841 | 1236 | O |
| B | — | — | — | 766 | 820 | O | 730 | 1060 | O |
| C | — | — | — | 426 | 595 | O | 410 | 590 | O |
| D | — | — | — | 2504 | 2515 | O | 2349 | 2361 | O |
| E | — | — | — | 599 | 2540 | O | 550 | 2332 | O |
| F | — | — | — | 297 | 1594 | O | 292 | 1327 | O |
| G | — | — | — | 12700 | 15600 | O | 11900 | 13400 | O |
| H | — | — | — | 10500 | 13000 | O | 9800 | 12400 | O |
| Comparative Example 3 | | | | | | | | | |
| A | 1580 | 4040 | X | — | — | — | — | — | — |
| B | 1143 | 1434 | X | — | — | — | — | — | — |
| C | 528 | 1093 | X | — | — | — | — | — | — |
| D | 9500 | 9900 | X | — | — | — | — | — | — |
| E | 1030 | 9730 | XX | — | — | — | — | — | — |
| F | 357 | 1752 | X | — | — | — | — | — | — |
| G | 43460 | 86000 | X | — | — | — | — | — | — |
| H | 16350 | 75000 | X | — | — | — | — | — | — |
| I | 4520 | — | — | 8270 | — | — | 7000 | — | — |
| J | 2010 | — | — | 7300 | — | — | 6100 | — | — |

Left column: viscosity just after preparation, center column: viscosity after four-week storage at −5° C., right column: appearance after six-time freezing at −20° C. for 2 hours and warming at room temperature
The appearance was represented by O no change, X partial increase of viscosity, and XX overall increase of viscosity and separation.
The viscosity unit is mPa·s.

Example 4

Glycerin or sucrose was added to an aqueous solution containing 35 weight percent of partially stearylated potassium phosphate with varied ratio ranging from 1 to 15 weight percent. The resultant aqueous compositions were tested in the same manner as in Example 3. The result is shown in Table 4.

TABLE 4

| Ratio | Glycerin | | | Sucrose | | |
|---|---|---|---|---|---|---|
| 0 | 1580 | 4040 | ½ | 1580 | 4040 | ½ |
| 1 | 1485 | 3653 | 1/3 | 1467 | 3575 | 1/3 |
| 2 | 1376 | 3247 | ¼ | 1355 | 3127 | 1/6 |
| 3 | 1255 | 2836 | ¼ | 1241 | 2698 | * |
| 4 | 1046 | 2259 | * | 1013 | 2077 | * |
| 5 | 1031 | 2124 | 0 | 976 | 1864 | 0 |
| 6 | 993 | 1946 | 0 | 925 | 1647 | 0 |
| 7 | 962 | 1789 | 0 | 880 | 1452 | 0 |
| 8 | 895 | 1576 | 0 | 841 | 1236 | 0 |
| 9 | 870 | 1500 | 0 | 820 | 1180 | 0 |
| 10 | 860 | 1470 | 0 | 806 | 1125 | 0 |
| 15 | 800 | 1300 | 0 | 769 | 1066 | 0 |

Left column: viscosity just after preparation, center column: viscosity after four-week storage at −5° C., right column: appearance after six-time freezing at −20° C. for 2 hours and warming at room temperature The figures in the right column represent the ratio of aqueous composition having increased viscosity. The asterisks represent that only a small part of the composition exhibited increased viscosity.

The viscosity unit is mPa·s.

The data in Table 4 shows even 1% of polyhydric alcohol is effective to decrease the viscosity of the aqueous composition. And 5% or more of polyhydric alcohol shows significant effect for preventing the increase of viscosity of the aqueous composition subjected to freezing.

Example 5 and Comparative Example 4.

The aqueous solutions were prepared by adding 2 to 8% (four levels) of glycerin or sucrose to the aqueous solution of the mixture of partially stearylated potassium phosphate and a nonionic surfactant (blended in 7:3). Each of the resultant solutions was applied to finish-free polyester fiber and their yarn spinning performance was tested. The result is shown in Table 5.

TABLE 5

| Additives and their ratio (%) | Static charge (kV) carding | Static charge (kV) drawing | Wraps on card cylinder (%) | Draft force of silver (g/g) | Roll wrap frequency in ring spinning |
|---|---|---|---|---|---|
| Example 5 | | | | | |
| Glycerin 2% | −0.05 | +0.17 | 49 | 79.8 | 100 |
| Glycerin 4% | −0.04 | +0.16 | 41 | 79.5 | 89 |
| Glycerin 6% | −0.04 | +0.13 | 35 | 79.6 | 81 |
| Glycerin 8% | −0.04 | +0.10 | 30 | 79.5 | 79 |
| Sucrose 2% | −0.05 | +0.28 | 39 | 77.8 | 73 |
| Sucrose 4% | −0.07 | +0.25 | 35 | 77.1 | 83 |
| Sucrose 6% | −0.09 | +0.25 | 27 | 79.3 | 113 |
| Sucrose 8% | −0.15 | +0.25 | 18 | 80.5 | 119 |
| Comparative Example 4 | | | | | |
| No additive | −0.05 | +0.35 | 53 | 82.2 | 103 |
| Glycerin 15% | −0.08 | +0.14 | 55 | 80.3 | 149 |
| Sucrose 15% | −0.37 | +0.30 | 13 | 81.3 | 165 |

Polyester fiber: 1.3 de 38 mm, 0.13% O.P.U. Sample size for testing: 20 g. Static charge was tested at 20° C. and 45% RH. Roll wrap frequency in ring spinning was tested at 30° C. and 65% RH. Others were tested at 20° C. and 65% RH. Roll wrap frequency was checked for 15 minutes.

The data in Table 5 shows polyhydric alcohol added 10% or less to partially stearylated potassium phosphate does not deteriorate they yarn spinning performance of the potassium phosphate.

As shown in Comparative example 4, polyhydric alcohol added more than 10% leads to increased roll wrap frequency in ring spinning.

Example 6 and Comparative Example 5

The aqueous solutions were prepared by adding glycerin or sucrose to the aqueous solution of the mixture of partially stearylated potassium phosphate and a nonionic surfactant (blended in 7:3). Each of the resultant solutions was applied to finish-free polyester filament and the friction between the filament and metal pin on which the filament was being driven was checked. The result is shown in Table 6.

TABLE 6

| Additives and their ratio | Yarn Speed 50 m/min | 100 m/min | 150 m/min | 200 m/min |
|---|---|---|---|---|
| Example 6 | | | | |
| Glycerin 2% | 41 | 50 | 54 | 56 |
| Glycerin 4% | 40 | 50 | 54 | 55 |
| Glycerin 6% | 39 | 48 | 53 | 56 |
| Glycerin 8% | 38 | 46 | 52 | 56 |
| Glycerin 10% | 38 | 46 | 53 | 56 |
| Sucrose 2% | 41 | 52 | 55 | 57 |
| Sucrose 4% | 42 | 53 | 56 | 58 |
| Sucrose 6% | 43 | 54 | 58 | 58 |
| Sucrose 8% | 45 | 56 | 60 | 62 |
| Comparative Example 5 | | | | |
| No additive | 41 | 51 | 55 | 56 |
| Sucrose 15% | 52 | 65 | 72 | 79 |

Polyester filament: 150 d/48f, 0.2% O.P.U. Initial tension $T_1$: 20 g

Friction pin: matte chrome pin
The filament to matte chrome pin friction was determined by subtracting initial tension ($T_1$) from final tension ($T_2$), both of which are represented by grams.

The data in Table 6 shows that 10% or less of polyhydric alcohol added to partially stearylated potassium phosphate does not give adverse effect on the frictional property of fiber applied with the potassium salt.

As shown in Comparative Example 5, more than 10% of sucrose added to the said phosphate leads to significant increase of fiber to metal friction.

As described above, the fiber finish of the present invention can provide a finish, which has low viscosity to attain improved handling and rarely increases its viscosity or separates during storage, without adverse effect on yarn spinning performance and frictional property of the fiber applied with the finish.

What is claimed is:

1. An aqueous composition of an alkali metal salt of partial alkyl esters of phosphoric acid characterized by containing 100 parts by weight of an alkali metal salt of partial alkyl esters of phosphoric acid having the following properties (1) to (3); (1) of which ester groups have linear or branched alkyl groups having 16 to 22 average carbon numbers, (2) of which degree of phosphorylation ranges from 0.6 to 1.0, and (3) of which degree of neutralization ranges from 60 to 100%; and by containing 1 to 10 parts by weight of $C_{3-12}$ polyhydric alcohol having three or more hydroxyl groups.

2. An aqueous composition in claim 1 wherein the said alkali metal salt of partial alkyl esters of phosphoric acid is a partially alkylated potassium phosphate.

3. An aqueous composition in claim 1 wherein the concentration of the said alkali metal salt of partial alkyl esters of phosphoric acid is 20 to 60 weight percent.

4. A method for stabilizing an aqueous solution of an alkali metal salt of partial alkyl esters of phosphoric acid characterized by adding 1 to 10 parts by weight of $C_{3-12}$ polyhydric alcohol having three or more hydroxyl groups to the aqueous solution of 100 parts by weight of an alkali metal salt of partial alkyl esters of phosphoric acid having the following properties (1) to (3); (1) of which ester groups have linear or branched alkyl groups having 16 to 22 average carbon numbers, (2) of which degree of phosphorylation ranges from 0.6 to 1.0, and (3) of which degree of neutralization ranges from 60 to 100%.

5. The method in claim 4 wherein the said alkali metal salt of partial alkyl esters of phosphoric acid is a partially alkylated potassium phosphate.

6. A fiber finish characterized by containing the aqueous composition in claim 1 as a major component.

* * * * *